United States Patent
Turner

(10) Patent No.: US 10,131,931 B2
(45) Date of Patent: Nov. 20, 2018

(54) RAPID DETERMINATION OF BACTERIAL SUSCEPTIBILITY TO AN ANTIBIOTIC AT THE POINT OF CARE

(71) Applicant: Ronald Turner, Norwich (GB)

(72) Inventor: Ronald Turner, Norwich (GB)

(73) Assignee: RONALD TURNER, Norwich (GB)

( * ) Notice: Subject to any disclaimer, the term of this patent is extended or adjusted under 35 U.S.C. 154(b) by 0 days.

(21) Appl. No.: 15/305,550

(22) PCT Filed: Apr. 20, 2015

(86) PCT No.: PCT/US2015/026580
§ 371 (c)(1),
(2) Date: Oct. 20, 2016

(87) PCT Pub. No.: WO2015/164225
PCT Pub. Date: Oct. 29, 2015

(65) Prior Publication Data
US 2017/0175161 A1    Jun. 22, 2017

Related U.S. Application Data

(60) Provisional application No. 61/983,800, filed on Apr. 24, 2014.

(51) Int. Cl.
*C12Q 1/04* (2006.01)
*C12Q 1/66* (2006.01)

(52) U.S. Cl.
CPC  *C12Q 1/04* (2013.01); *C12Q 1/66* (2013.01)

(58) Field of Classification Search
None
See application file for complete search history.

(56) References Cited

U.S. PATENT DOCUMENTS

| 9,562,253 | B1 * | 2/2017 | Turner | C12Q 1/04 |
| 2012/0301907 | A1 * | 11/2012 | Sellappan | G01N 21/76 |
| | | | | 435/8 |
| 2013/0189717 | A1 * | 7/2013 | Bugler | C12Q 1/06 |
| | | | | 435/8 |

OTHER PUBLICATIONS

Lafond, M. et al. A Comparison of Three Rapid and Accurate Bioluminescent Antibiotic Susceptibility Tests. J of Pharmacological and Toxicological Methods 61(1)16-19, 2010. (Year: 2010).*

* cited by examiner

*Primary Examiner* — Ralph J Gitomer
(74) *Attorney, Agent, or Firm* — James S. Keddie; Bozicevic, Field & Francis LLP

(57) ABSTRACT

A method for determining whether bacteria in a sample obtained from a subject at a point of care in a clinical setting is susceptible to an antibiotic, within a time period associated with a point of care. The method includes measuring a bioluminescent indication from a first test sample based on released ATP to determine a characteristic associated with the bioluminescent indication and comparing the characteristic associated with the bioluminescent indication to a first threshold. The method includes determining whether a bacteria is present by comparing the difference between a characteristic associated with a first confirmatory bioluminescent signal and a characteristic associated with a second confirmatory bioluminescent signal to an confirmatory threshold. The method includes determining that bacteria is susceptible to an antibiotic by comparing a difference between a characteristic associated with a second bioluminescent signal and a characteristic associated with the first bioluminescent signal to a second threshold.

8 Claims, 5 Drawing Sheets

RAPID DETERMINATION OF BACTERIAL SUSCEPTIBILITY TO AN ANTIBIOTIC AT THE POINT OF CARE

BACKGROUND

Medical practitioners such as doctors, veterinarians, etc. often prescribe antibiotics for subjects (e.g., humans or animals) exhibiting symptoms that are attributable to a bacterial infection, but are not actually suffering from a bacterial infection. In such cases, the patient may exhibit symptoms that are attributable to non-bacterial causes such as viral infections, etc. for which antibiotics are not an effective remedy. Furthermore, prescribing antibiotics in such cases may contribute to the growing problem of over-prescribing of antibiotics, which enable certain bacterial strains to become increasingly resistant to antibiotics.

Additionally, when the patient is suffering from a bacterial infection, medical practitioners often prescribe an antibiotic that is not an effective treatment against a particular bacterial infection from which the patient is suffering and is thus not an effective remedy for the infection or treating the symptoms. Ineffective antibiotics and/or incompletion and non-compliance with prescribed treatment also contributes to increasing bacterial resistance Many devices and assays are available that can determine whether or not the subject is suffering from a bacterial infection and, if so, to identify an antibiotic that is susceptible to the bacterial infection. However, such devices and assays cannot be used at the point of care because the complexity of the devices and assays require specialized training by laboratory personnel and expensive equipment employ the devices or perform the assays. Additionally, such assays include growing cultures, incubation, or procedures that are to be performed within a period of time (e.g., hours, days, etc.) that makes performing the assay at the point of care, such as during a typical visit to the doctor's office or veterinarian (e.g., usually within 30 to 60 minutes), impractical.

SUMMARY

According to one implementation, described herein, a method for determining, within a time period associated with a point of care visit in a clinical setting, whether a sample, obtained from a subject at the point of care, includes a bacterial infection, may include applying, at a first time, to a portion of the sample, a first reagent to create a first test sample from which non-bacteria based background Adenosine triphosphate (ATP) has been removed by the first reagent. The method may further include incubating the first test sample for a first time period and applying a second reagent to the first test sample to release ATP from bacterial cells when the first test sample includes bacterial cells. The method may yet further include measuring a bioluminescent indication from the first test sample based on released ATP to determine a characteristic associated with the bioluminescent indication and determining whether the sample includes the bacterial infection by comparing the characteristic associated with the bioluminescent indication to a first threshold. The method further include comparing the characteristic associated with the bioluminescent indication to a confidence threshold. The method may further include applying, to at least a portion of the sample, the first reagent and a culture medium to create a first confirmatory test sample and a second confirmatory test sample from which non-bacteria based background ATP has been removed by the first reagent. The method may yet further include incubating the first confirmatory test sample for a first confirmatory time period and at a first temperature and the second confirmatory test sample for a second confirmatory time period that is greater than the first confirmatory time period and at a second temperature. The method may include applying the second reagent to the first confirmatory test sample at the end of the first confirmatory time period and to the second confirmatory test sample at the end of the second confirmatory time period, to release ATP from bacterial cells when the first confirmatory test sample and second confirmatory test sample include bacterial cells. The method may further include measuring a first confirmatory bioluminescent signal from the first confirmatory test sample based on released ATP to determine a characteristic associated with the first confirmatory bioluminescent signal and a second confirmatory bioluminescent signal from the second confirmatory test sample based on released ATP to determine a characteristic associated with the second confirmatory bioluminescent signal. The method may yet further include determining a difference between the characteristic associated with the first confirmatory bioluminescent signal and the characteristic associated with the second confirmatory bioluminescent signal. Furthermore, the method may include determining, at a second time, whether the bacterial infection is present in the sample by comparing the difference between the characteristic associated with the first confirmatory bioluminescent signal and the characteristic associated with the second confirmatory bioluminescent signal to an confirmatory threshold. A difference between the first time and the second time being less than the time period associated with the point of care visit.

According to another implementation, describe herein, a method for determining whether bacteria in a sample obtained from a subject at a point of care in a clinical setting is susceptible to an antibiotic, within a time period associated with a point of care, may include applying, at a first time, to a portion of the sample, a first reagent to create a first test sample from which non-bacteria based background Adenosine triphosphate (ATP) has been removed by the first reagent. The method may further include incubating the first test sample for a first time period and applying a second reagent to the first test sample to release ATP from bacterial cells when the first test sample includes bacterial cells. The method may yet further include measuring a bioluminescent indication from the first test sample based on released ATP to determine a characteristic associated with the bioluminescent indication and determining whether the sample includes the bacterial infection by comparing the characteristic associated with the bioluminescent indication to a first threshold. The method may include applying, to at least a portion of the sample, the first reagent and a culture medium to create a second test sample and a third test sample, from which non-bacteria based background ATP has been removed by the first reagent. The method may further include applying a first antibiotic to the third test sample, incubating the second test sample and the third test sample for a second time period and at a first temperature, and applying a second reagent to the second test sample and the third test sample at the end of the second time period. The method may yet further include measuring a first bioluminescent signal from the second test sample based on released ATP to determine a characteristic associated with the first bioluminescent signal and a second bioluminescent signal from the third test sample based on released ATP to determine a characteristic associated with the second bioluminescent signal. The method may include determining a difference between the characteristic associated with the first bioluminescent signal and the characteristic associated with the second bioluminescent signal and determining, at a third time, that the bacterial infection is susceptible to the first antibiotic by comparing the difference between the characteristic associated with the second bioluminescent signal and the characteristic associated with the first bioluminescent signal to a second threshold. A difference between the first time and the third time being less than the time period associated with the point of care visit.

According to yet another implementation, described herein, a method for determining whether bacteria in a sample obtained from a subject at a point of care in a clinical setting is susceptible to an antibiotic, within a time period associated with a point of care, may include applying, at a first time, to a portion of the sample, a first reagent to create a first test sample from which non-bacteria based background Adenosine triphosphate (ATP) has been removed by the first reagent. The method may further include incubating the first test sample for a first time period and applying a second reagent to the first test sample to release ATP from bacterial cells when the first test sample includes bacterial cells. The method may yet further include measuring a bioluminescent indication from the first test sample based on released ATP to determine a characteristic associated with the bioluminescent indication. The method may include determining whether the sample includes the bacterial infection by comparing the characteristic associated with the bioluminescent indication to a first threshold and comparing the characteristic associated with the bioluminescent indication to a confidence threshold. The method may include applying, to at least a portion of the sample, the first reagent and a culture medium to create a first confirmatory test sample and a second confirmatory test sample from which non-bacteria based background ATP has been removed by the first reagent. The method may further include incubating the first confirmatory test sample for a first confirmatory time period and at a first temperature and the second confirmatory test sample for a second confirmatory time period that is greater than the first confirmatory time period and at a second temperature. The method may yet further include applying the second reagent to the first confirmatory test sample at the end of the first confirmatory time period and the second confirmatory test sample at the end of the second confirmatory time period, to release ATP from bacterial cells when the first confirmatory test sample and second confirmatory test sample include bacterial cells. The method may include measuring a first confirmatory bioluminescent signal from the first confirmatory test sample based on released ATP to determine a characteristic associated with the first confirmatory bioluminescent signal and a second confirmatory bioluminescent signal from the second confirmatory test sample based on released ATP to determine a characteristic associated with the second confirmatory bioluminescent signal. The method may further include determining a difference between the characteristic associated with the first confirmatory bioluminescent signal and the characteristic associated with the second confirmatory bioluminescent signal. The method may yet further include determining, at a second time, whether the bacterial infection is present in the sample by comparing the difference between the characteristic associated with the first confirmatory bioluminescent signal and the characteristic associated with the second confirmatory bioluminescent signal to a confirmatory threshold. A difference between the first time and the second time being less than the time period associated with the point of care visit. The method may include applying, to at least a portion of the sample, the first reagent and a culture medium to create a second test sample and a third test sample, from which non-bacteria based background ATP has been removed by the first reagent. The method may further include applying a first antibiotic to the third test sample, incubating the second test sample and the third test sample for a second time period and at a third temperature, and applying a second reagent to the second test sample and the third test sample at the end of the second time period. The method may yet further include measuring a first bioluminescent signal from the second test sample based on released ATP to determine a characteristic associated with the first bioluminescent signal and a second bioluminescent signal from the third test sample based on released ATP to determine a characteristic associated with the second bioluminescent signal. The method may include determining a difference between the characteristic associated with the first bioluminescent signal and the characteristic associated with the second bioluminescent signal, and determining, at a third time, that the bacterial infection is susceptible to the first antibiotic by comparing the difference between the characteristic associated with the second bioluminescent signal and the characteristic associated with the first bioluminescent signal to a second threshold. A difference between the first time and the third time being less than the time period associated with the point of care visit.

DETAILED DESCRIPTION OF PREFERRED EMBODIMENTS

The following detailed description refers to the accompanying drawings. The same reference numbers in different drawings may identify the same or similar elements.

The systems, methods, technologies, and/or techniques (hereinafter referred to as the "systems and/or methods"), described herein, may enable one or more assays to be performed on a sample, obtained from a subject (e.g., human or animal) to detect a bacterial infection and/or to determine antibiotic susceptibility, to the bacterial infection, when the bacterial infection is detected in the sample. The one or more assays can be performed, by a medical practitioner (e.g., a doctor, veterinarian, nurse, physician's assistant, a trained point of care operator, etc.), within a period of time (e.g., 30 to 60 minutes) that enables such assays to be performed at the point of care in a clinical setting (e.g., during a typical doctor's office visit, veterinary visit, etc.). Enabling the detection of a bacterial infection and/or the identification of an antibiotic effective in treating the infection at the point of care in a clinical setting may reduce the occurrence of prescribing antibiotics for non-bacterial ailments, decrease the occurrence of prescribing ineffective antibiotics, and reduce suffering from the subject by prescribing antibiotics that are effective in treating the bacterial infection. Additionally, or alternatively, the systems and/or methods may include a kit that enables the medical practitioner to perform the one or more assays, at the point of care in a clinical setting, without using expensive and/or complex equipment, sending the samples off to a laboratory, or culturing the samples over a longer period of time (typically 48-72 hours) that exceeds the time period that is typical for a point of care visit.

The term "point of care," as used herein, is akin to a period of time (e.g., usually between 30-60 minutes) during which an office visit occurs between a medical practitioner (e.g., a doctor, veterinarian, nurse, physician's assistant, a trained point of care operator, etc.) (hereinafter, a "practitioner") and a subject during which the sample can be collected, one or more assay performed, and the results obtained without the time and expense of sending the sample to a laboratory for testing. The term "clinical setting" as used herein, generally refers to a site at which patients are examined and treated by a practitioner.

The systems and/or methods are described herein with respect to pathological bacteria in a urine sample for explanatory purposes. Additionally, or alternatively, the systems and/or methods may be used with respect to pathological bacteria within other types of body fluid samples, such as blood or constituents thereof, wound exudate, cerebro-spinal fluid, vaginal fluid, mouth or throat, etc.

Figure 1:
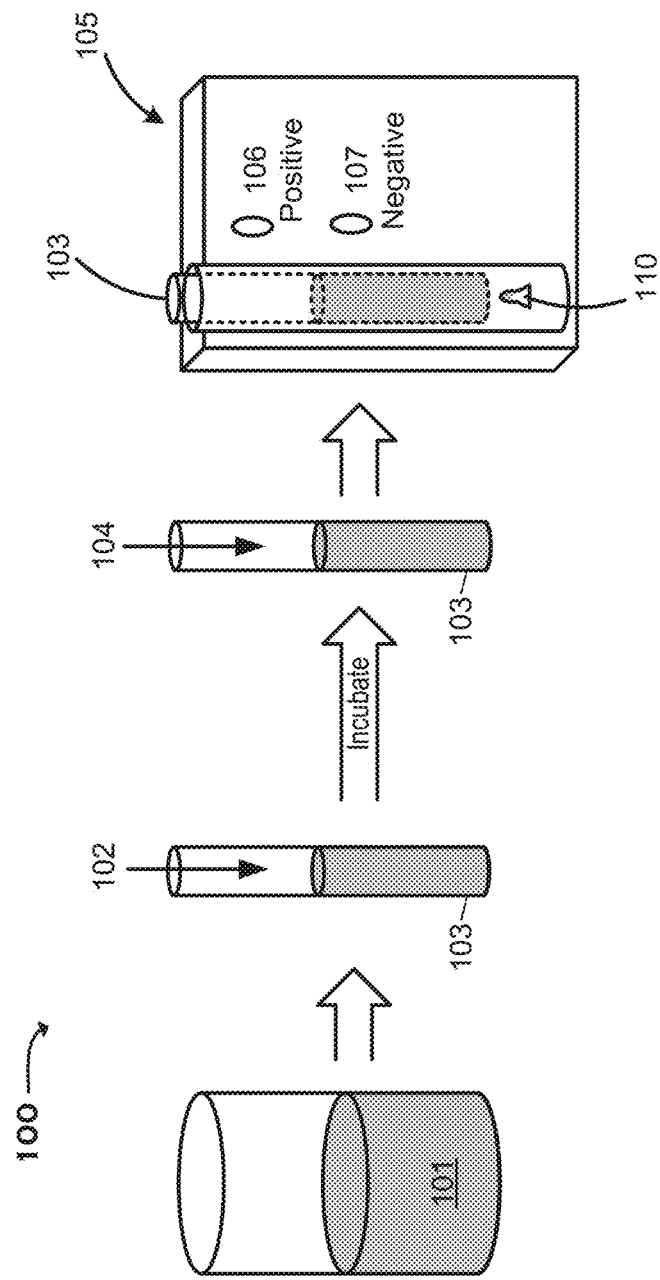
FIG. 1 is a diagram of an example assay performed on a sample obtained from a subject to detect the presence of a bacterial infection.

FIG. 1 is a diagram of an example assay 100 that may be performed on sample 101 obtained from a subject to detect the presence of a bacterial infection. As illustrated in FIG. 1, assay 100 may be performed on sample 101 obtained from a subject (e.g., a human subject, an animal subject, etc.) to determine whether sample 101 includes bacterial cells that may indicate that the subject is suffering from a bacterial infection. Assay 100 may be completed (e.g., such that the presence of a bacterial infection may be determined) within a time period (e.g., ~1 to 10 minutes) (e.g., $T_{100}$) that is less than a time period associated with a point of care visit ($T_{100} < T_{POC}$). In one example, the quantity of bacterial cells that indicates that the subject is suffering from the bacterial infection, may correspond to a clinically significant level of bacterial cells (e.g., 1000 to 10,000 colony forming units/milliliter (cfu/ml, depending on bacterial virulence and type of sample (animal; human; cystocentesis; clean-catch)) in a urinary tract infection in humans or animals) at which the subject exhibits symptoms, associated with the bacterial infection, that are readily investigated by a medical practitioner at the point of care. The clinically significant level may be different depending on the subject (e.g., animal, human, type of animal, size of subject, age of subject, gender of subject, etc.).

A first reagent 102 may be applied to all or a portion of sample 101 to create a test sample 103 and/or may incubate test sample 103. Additionally, or alternatively, a first test sample 103 may include all or a portion of sample 101 (e.g., 1 to 20 microliters (μL)) and first reagent 102 (e.g. 100 to 500 μL). First reagent 102 may cause non-bacterial Adenosine Triphosphate (ATP) (e.g., background ATP released from somatic cells within the sample, free ATP released from contaminants or other non-bacterial sources within the sample, etc.) to be removed from first test sample 103. The time period of incubation (e.g., a first incubation period shown as $T_{INC1}$ in FIG. 1) may be less than a first time period (e.g., ~1 to 15 minutes) (e.g., T1), which is less than the time period associated with a typical point of care visit (e.g., $T_{INC1} < T_1 < T_{POC}$, where $T_{POC}$ corresponds to the time period of a typical point of care visit). As described herein, the point of care time period may be less than sixty (60) minutes.

First reagent 102 (e.g., 50 to 500 μL) may, for example, include one or more first constituent and/or one or more ingredients that causes cell walls, associated with somatic cells of the subject, to breakdown, become permeable or to otherwise permit background ATP therein to be released. The first constituent mixture may include Antiseptics and/or Detergents, including but not limited to asolectin-CHAPS ((3-[(3 cholamidopropylpropanesulfonic acid) (e.g., 0.05 to 0.5%), benzalkonium chloride (e.g., 0.01 to 0.05%), benzethonium chloride (e.g., 0.0001 to 0.1%), benzyl chloride (e.g., 0.001 to 0.1%), cetalkonium chloride (e.g., 0.001 to 0.5%), cetrimide (e.g., 0.001 to 0.01%), cetrimonium bromide (e.g., 0.001 to 0.05%), cetylpyridinium chloride (e.g., 0.01 to 0.5%), cetyltrimethylammonium bromide (e.g., 0.001 to 0.05%), Chlorhexidine digluconate (e.g., 0.001 to 0.1%), Chlorhexidine diacetate (e.g., 0.001 to 0.02%), CTAB (hexadecyltrimethyl ammonium bromide (e.g., 0.001 to 0.1%), didecyldimethylammonium chloride (e.g., 0.001 to 0.1%), dofanium chloride (e.g., 0.001 to 0.1%), domiphen bromide (e.g., 0.01 to 0.1%), hexadecyltrimethylammonium bromide (e.g., 0.001 to 0.1%), methylbenzethonium chloride (e.g., 0.001 to 0.1%), NRM (e.g., 0.001 to 0.005%), palmityltrimethylammonium bromide (e.g., 0.001 to 0.1%), Sodium dodecyl sulfate (e.g., 0.001 to 0.005%), teraethylammonium bromide (e.g., 0.0001 to 0.01%), Tween 20 (e.g., 0.001 to 0.1%) and/or Tween 80 (e.g., 0.01 to 0.1%). For example, in one implementation first reagent 102 may include 10 to 100 nM Tris Acetate buffer, 0.0001 to 0.1% Benzethonium Chloride, and 0.5 to 4 Units/ml of hydrolyzing enzyme.

First reagent 102 may also, or alternatively, include one or more second constituent mixture and/or one or more ingredient that causes the non-bacterial and free in solution ATP to be removed from first test sample 103. Such removal may, for example, be caused by hydrolyzing the non-bacterial ATP. The second constituent mixture may include hydrolytic enzymes, including but not limited to Adenylate kinase (Myokinase) (e.g., 50 to 500 Units/ml), Apyrase (e.g., 0.1 to 5 Units/ml), ATP synthase (e.g., 0.1 to 5 mg/ml), ATPase (e.g., 0.1 to 5 Units/ml), and/or urea amidohydrolase (e.g., 1 to 10 Units/ml).

Additionally, or alternatively, second reagent 104 (e.g., 100 to 500 μL) may be added to first test sample 103. Second reagent 104 may include one or more third constituent that causes the cell walls of any bacterial cells within first test sample 103 to breakdown, become permeable, or otherwise permit bacterial ATP to be released from the bacterial cells when sample 101 includes bacterial cells. The third constituent mixture may include antiseptics and/or detergents, including but not limited to asolectin-CHAPS ((3-[(3 cholamidopropylpropanesulfonic acid) (e.g., 0.5 to 5.0%), benzalkonium chloride (e.g., 0.1 to 0.5%), benzethonium chloride (e.g., 0.01 to 0.1%), benzyl chloride (e.g., 0.01 to 1.0%), cetalkonium chloride (e.g., 0.1 to 5%), cetrimide (e.g., 0.01 to 0.2%), cetrimonium bromide (e.g., 0.1 to 0.5%), cetylpyridinium chloride (e.g., 0.1 to 1.0%), cetyltrimethylammonium bromide (e.g., 0.1 to 0.5%), chlorhexidine digluconate (e.g., 0.1 to 1.0%), chlorhexidine diacetate (e.g., 0.1 to 0.5%), CTAB (hexadecyltrimethyl ammonium bromide) (e.g., 0.1 to 0.5%), didecyldimethylammonium chloride (e.g., 0.1 to 0.5%), dofanium chloride (e.g., 0.1 to 0.5%), domiphen bromide (e.g., 0.1 to 0.5%), hexadecyltrimethylammonium bromide (e.g., 0.1 to 0.5%), methylbenzethonium chloride (e.g., 0.01 to 1.0%), NRM (e.g., 0.01 to 0.05%), palmityltrimethylammonium bromide (e.g., 0.01 to 0.5%), Sodium dodecyl sulfate (e.g., 0.01 to 0.05%), teraethylammonium bromide (e.g., 0.01 to 0.05%), Tween 20 (e.g., 0.01 to 0.5%), and/or Tween 80 (e.g., 0.1 to 0.5%).

First reagent 102 and/or second reagent 104 may also, or alternatively, include one or more fourth constituent that corresponds to a certain buffer that maintains and/or controls the acidity and/or alkalinity (e.g., pH) and integrity of the mixture of the first test sample 103 and second reagent 104 to minimize the mortality of the bacterial cells (if any) within the mixture. The fourth constituent mixture may include buffering agents, including but not limited to MOPS (e.g., 50 to 500 mM), xMAP sheath fluid (e.g., 50 to 500 mM), Phosphate buffered saline (PBS) (e.g., 50 to 500 mM), Tris acetate EDTA (e.g., 20 to 100 mM), Tris Borate (e.g., 20 to 100 mM), Tris—EDTA (e.g., 20 to 100 mM), Trisglycine (e.g., 20 to 100 mM), Trizma base (e.g., 50 to 500 mM), xMAP sheath fluid (e.g., 20 to 200 mM), Magnesium Acetate Tetrahydrate (e.g., 5 to 50 mM), Sorbitol (e.g., 100 to 500 g/L), Bovine Serum Albumin (e.g., 0.1 to 0.5 g/L), Magnesium Chloride (e.g., 2 to 20 mM), Magnesium sulfate (e.g., 2 to 50 mM), HEPES (4-(2-Hydroxyethyl)piperazine-1-ethanesulfonic acid (e.g., 20 to 100 mM), N-(2-Hydroxyethyl)piperazine-N'-(2-ethanesulfonic acid) (e.g., 10 to 50 mM).

Additionally, or alternatively, second reagent 104 may be added to first test sample 103 to react with the released bacterial ATP and/or to cause light (hereinafter, a "bioluminescent indication") to be emitted from the mixture. Second reagent 104 may include one or more fifth constituent that reacts with the released bacterial ATP to emit a bioluminescent indication, a characteristic (e.g., strength, intensity, etc.) of which (e.g., "L") may be proportional to the quantity of bacterial ATP released from the bacterial cells. The fifth constituent mixture may include Bioluminescence compounds, including but not limited to Luciferin (e.g., 5 to 30 mg/L), and/or Luciferase (e.g., firefly luciferase, etc.) (e.g., 5 to 30 mg/L).

Additionally, or alternatively, the quantity of bacterial ATP may be proportional to the quantity of bacterial cells from which the bacterial ATP was released. Thus, the characteristic (e.g., strength, intensity, etc.) associated with the bioluminescent indication (e.g., L) (and/or its associated characteristics) may be proportional to the quantity of bacterial cells in first test sample 103. The bioluminescent indication (e.g., L) may be detected and/or measured using test device 105 (e.g., a luminometer, a photodetector, a photodiode, handheld device, non-handheld device, and/or any device capable of detecting the emitted light). By way of example, second reagent 104 may be added to first test sample 103 and first test sample 103 may be inserted into test device 105 (e.g., including detection mechanism 110). Test device 105 may output first indication 106 (e.g., a positive indication, etc.) when the bioluminescent indication is detected and/or a characteristic (e.g., signal strength) associated with the bioluminescent indication, for example based on a measure of light intensity, luminescence, etc. (e.g., lumens (lm), candelas, footcandles (fc), lux, relative light units (RLU's), etc.), is greater than a first threshold (e.g., L>TH1, where TH1 corresponds to the first threshold) (e.g., TH1 may be 30,000 to 5 million RLU's) which may indicate bacterial cells exist within sample 101 at a clinically significant level. Test device 105 may output a second, different indication 107 (e.g., a negative indication, etc.) when the bioluminescent indication (e.g., L) is not detected and/or a characteristic (e.g., 0 to 30,000 RLU's) associated with the bioluminescent indication is not greater than the first threshold, which may indicate that the bacterial cells do not exist within sample 101 at a clinically significant level. Additionally, or alternatively, test device 105 may indicate a characteristic (e.g., strength, intensity, etc.) associated with the bioluminescent indication to allow comparison with a first threshold.

In the event that indication 107 (e.g., a negative indication, etc.) is outputted by test device 105 (e.g., when L≤TH1), a medical practitioner may decide not to prescribe antibiotics to the subject, which may preclude over-prescribing antibiotics when the subject is not suffering from a bacterial infection. In the event that indication 106 (e.g., a positive indication, etc.) is outputted by test device 105, another assay (e.g., assay 200 of FIG. 2) may be performed on sample 101 to determine whether an antibiotic is susceptible to the bacterial infection within sample 101, as described below with respect to FIG. 2. Additionally, or alternatively, a confirmatory assay may be performed on sample 101 to further determine whether a clinically significant level of the bacterial cells exist or do not exist within sample 101, as described below with respect to FIG. 4. Additionally, or alternatively, a characteristic associated with the bioluminescent indication may indicate and/or correspond to a severity of a bacterial infection, which may, for example, assist in prescribing an antibiotic.

The number of reagents, constituents, buffers, and/or components, illustrated in FIG. 1, is provided for explanatory purposes only and is not intended to be so limited. Additionally, or alternatively, assay 100 may include additional reagents, constituents, buffers, and/or components; fewer reagents, constituents, buffers, and/or components; different reagents, constituents, buffers, and/or components; or differently arranged reagents, constituents, buffers, and/or components than illustrated in FIG. 1.

Figure 2:
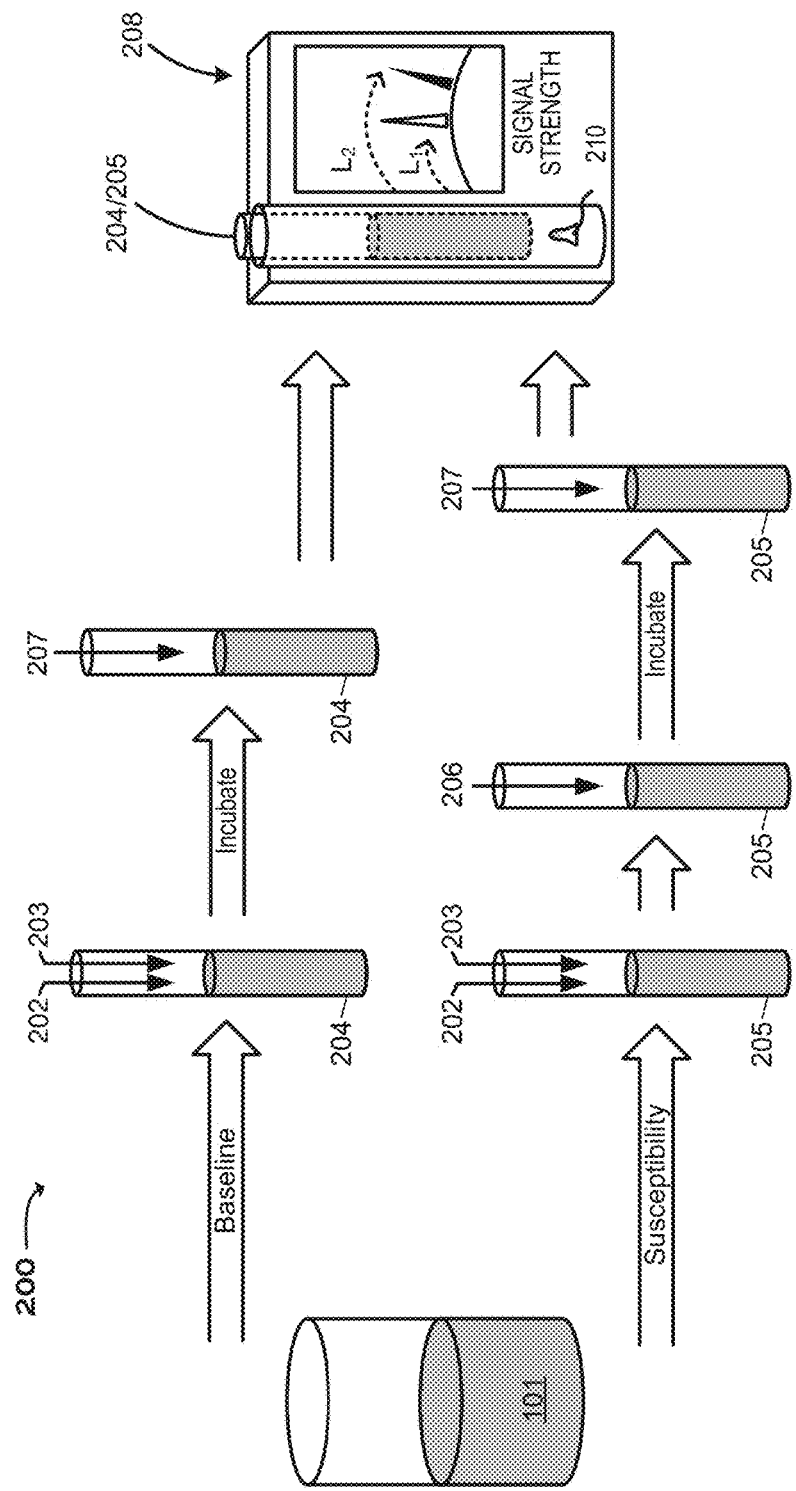
FIG. 2 is a diagram of an example assay performed on a sample obtained from a subject to detect the susceptibility of a bacterial infection to one or more antibiotic.

FIG. 2 is a diagram of example assay 200 that may be performed on sample 101 obtained from a subject to detect the susceptibility of a bacterial infection to one or more antibiotics. Assay 200 may be completed (e.g., such that the susceptibility of a bacterial infection may be determined) within a time period (e.g., $T_{200}$) (e.g., ~20≤$T_{200}$<60 minutes) that is less than a time period associated with a point of care visit ($T_{200}$<$T_{POC}$). Additionally, or alternatively, both assay 100 and assay 200 may be completed within a time period that is less than a time period associated with a point of care visit ($T_{100}$+$T_{200}$<$T_{POC}$).

In one example, assay 200 may be performed on one or more pretreated samples from which non-bacterial ATP (e.g., background ATP, free ATP, etc.) have been removed in a manner similar to that described in FIG. 1. Additionally, or alternatively, assay 200 may be performed on sample 101 in a manner described below.

For example, first reagent 202 (e.g., 50 to 400 μL) and/or culture medium 203 (e.g., 50 to 300 μL) may be added to a portion of test sample 101 (e.g., 10 to 100 μL) to create a second test sample 204 and a third test sample 205. In one example, second test sample 204 and third test sample 205 may be of approximately equal volume (e.g., 100 to 400 μL) to ensure that the concentration of any reagents, buffers, culture medium, etc. added to second test sample 204 and third test sample 205 are approximately equal between second test sample 204 and third test sample 205. First reagent 202 may, in a manner similar to that described above with respect to FIG. 1, cause non-bacterial ATP to be released and removed from second test sample 204 and third test sample 205. Culture medium 203 may promote the growth and robustness of the bacterial population (e.g., comprised of bacterial cells) within second test sample 204 and third test sample 205. Culture medium 203 may include Culture Media compounds, including but not limited to A1Broth (e.g., 50 to 300 μL), Andrade Peptone Water (e.g., 50 to 300 μ), Blood Agar (Base) (e.g., 50 to 300 μL), BRILA MUG Broth (e.g., 50 to 300 μL), Brilliant Green Bile Lactose Broth (e.g., 50 to 300 μL), Bromcresol Purple Broth (e.g., 50 to 300 μL), China Blue Lactose Agar (e.g., 50 to 300 μL), Chocolate agar (e.g., 50 to 300 μL), Christensen's Urea Agar (e.g., 50 to 300 μ), CLED Agar (e.g., 50 to 300 μL), Decarboxylase Broth Base (e.g., 50 to 300 μL), Moeller (e.g., 50 to 300 μL), DEV ENDO Agar (e.g., 50 to 300 μL), DEV Lactose Peptone Broth (e.g., 50 to 300 μL), DEV Tryptophan Broth (e.g., 50 to 300 μL), EC Broth (e.g., 50 to 300 μL), ECD Agar (e.g., 50 to 300 μL), ECD MUG Agar (e.g., 50 to 300 μL), EMB Agar (e.g., 50 to 300 μL), Endo Agar (e.g., 50 to 300 μL), ENDO Agar (Base) (e.g., 50 to 300 μL), Gassner Agar (e.g., 50 to 300 μL), Glucose Bromcresol Purple Agar (e.g., 50 to 300 μL), HiCrome™ Coliform Agar (e.g., 50 to 300 μL), HiCrome™ E. coli Agar B (e.g., 50 to 300 μL), HiCrome™ ECC Agar (e.g., 50 to 300 μL), HiCrome™ ECC Selective Agar (e.g., 50 to 300 μL), HiCrome™ ECD Agar with MUG (e.g., 50 to 300 μL), HiCrome™ M-TEC Agar (e.g., 50 to 300 μL), HiCrome™ Mac Conkey Sorbitol Agar (e.g., 50 to 300 μL), HiCrome™ MM Agar (e.g., 50 to 300 μL), HiCrome™ Rapid Coliform Broth (e.g., 50 to 300 μL), HiCrome™ UTI Agar (e.g., 50 to 300 μL), modified, Kligler Agar (e.g., 50 to 300 μL), Lactose Broth (e.g., 50 to 300 μL), Lactose Broth (e.g., 50 to 300 μL), Lactose TTC Agar with Tergitol®-7 (e.g., 50 to 300 μL), Lauryl sulphate Broth (e.g., 50 to 300 μL), Levine EMB Agar (e.g., 50 to 300 μL), LST-MUG Broth (e.g., 50 to 300 μL), Lysine Iron Agar (e.g., 50 to 300 μL), M Endo Broth (e.g., 50 to 300 μL), M HD Endo Broth with Brilliant Green (e.g., 50 to 300 μL), m-Endo Agar LES (e.g., 50 to 300 μL), M-FC Agar (e.g., 50 to 300 μL), m-FC Agar Plates (55 mm diameter) (e.g., 50 to 300 μL), M-FC Agar (e.g., 50 to 300 μL), Vegitone (e.g., 50 to 300 μL), M-Lauryl Sulphate Broth (e.g., 50 to 300 μL), M-Lauryl Sulphate Broth (e.g., 50 to 300 μL), Vegitone (e.g., 50 to 300 μL), Mac Conkey Agar No. 1 (e.g., 50 to 300 μL), Mac Conkey Agar No. 1 (e.g., 50 to 300 μL), Vegitone (e.g., 50 to 300 μL), MacConkey Agar with Crystal Violet (e.g., 50 to 300 μL), Sodium Chloride and 0.15% Bile Salts (e.g., 50 to 300 μL), MacConkey Broth (e.g., 50 to 300 μL), MacConkey Broth purple (e.g., 50 to 300 μL), MacConkey MUG Agar (e.g., 50 to 300 μL), MacConkey-Agar (without salt) (e.g., 50 to 300 μL), MacConkey-Sorbitol Agar (e.g., 50 to 300 μL), Malonate Broth (e.g., 50 to 300 μL), Membrane Lactose Glucuronide Agar (e.g., 50 to 300 μL), Methyl Red Voges Proskauer Broth (e.g., 50 to 300 μL), Methyl Red Voges Proskauer Saline Broth (e.g., 50 to 300 μL), Mineral-modified Glutamate Broth (Base) (e.g., 50 to 300 μL), Mossel Broth (e.g., 50 to 300 μL), Motility Test Medium (e.g., 50 to 300 μL), Mucate Broth (e.g., 50 to 300 μL), MUG EC Broth (e.g., 50 to 300 μL), MUG Tryptone Soya Agar (e.g., 50 to 300 μL), Nitrate Broth (e.g., 50 to 300 μL), OF Test Nutrient Agar (e.g., 50 to 300 μL), Plate Count MUG Agar (e.g., 50 to 300 μL), Simmons Citrate Agar (e.g., 50 to 300 μL), TBX Agar (e.g., 50 to 300 μL), Tergitol®-7 Agar (e.g., 50 to 300 μL), Triple Sugar Iron Agar (e.g., 50 to 300 μL), Tryptone Medium (e.g., 50 to 300 μL), Tryptone Water (e.g., 50 to 300 μL), Tryptone Water (e.g., 50 to 300 μL), Vegitone (e.g., 50 to 300 μL), Urea Broth (e.g., 50 to 300 μL), Vegitone (e.g., 50 to 300 μL), Violet Red Bile Agar (e.g., 50 to 300 μL), Violet Red Bile Agar (e.g., 50 to 300 μL), Vegitone (e.g., 50 to 300 μL), Violet Red Bile Glucose Agar (e.g., 50 to 300 μL), Violet Red Bile Glucose Agar without Lactose (e.g., 50 to 300 μL), Violet Red Bile Glucose Agar without Lactose (e.g., 50 to 300 μL), Vegitone (e.g., 50 to 300 μL), Violet Red Bile Lactose Dextrose Agar (e.g., 50 to 300 μL), VRB MUG Agar (e.g., 50 to 300 μL), WL Differential Agar (e.g., 50 to 300 μL), and/or XLT4 Agar (Base) (e.g., 50 to 300 μL). For example, in one implementation first reagent 202 may include 10 to 100 nM Tris Acetate buffer, 0.0001 to 0.1% Benzethonium Chloride, and 0.5 to 4 Units/ml of hydrolyzing enzyme and/or culture medium 203 may include 50 to 300 μL of Tryptic Soy Broth. Additionally, or alternatively, second test sample 204 may correspond to a baseline sample.

First antibiotic 206 (e.g., Amoxicillin) (e.g., 10 to 100 μg) may also, or alternatively, be added to third test sample 205 in a manner that causes a concentration level of first antibiotic 206, within test sample 205, to be approximately equal to a concentration level that first antibiotic 206 would approach in, for example, urine of the subject after being ingested, digested, and/or metabolized by the subject. With respect to implementations in which sample 101 is based on other than the urine of the subject (e.g., blood, wound exudate, optical fluid, cerebro—spinal fluid, vaginal fluid, mouth or throat, etc.) the concentration of first antibiotic 206, within test sample 205, may correspond to the concentration that first antibiotic 206 would approach in the urine, blood, wound exudate, optical fluid, etc. cerebro—spinal fluid, etc. of the subject after being ingested, digested, and/or metabolized by the subject.

Additionally, or alternatively, second test sample 204 and/or third test sample 205 may be incubated for a second incubation time period (e.g., $T_{INC2}$). The time period of incubation (e.g., $T_{INC2}$) may be less than a second time period (e.g., ~20 to 40 minutes) (e.g., T2), which may be less than the time period associated with a typical point of care visit (e.g., $T_{INC2} < T_2 < T_{POC}$). Additionally, or alternatively, the total time for incubation (e.g., with respect to assay 100 of FIG. 1 and assay 200 of FIG. 2) may be less than the time period associated with the typical point of care visit (e.g., $T_{INC1} + T_{INC2} < T_{POC}$).

Second reagent 207 (e.g., 100 to 500 μL) may, in a manner similar to that described above with respect to assay 100 of FIG. 1, be added to second test sample 204 and third test sample 205 to release the bacterial ATP from the bacterial cells therein and to cause bioluminescent light to be emitted from each of second test sample 204 and/or third test sample 205. Test device 208 (e.g., a luminometer, a photodetector, a photodiode, handheld device, non-handheld device, or any device capable of measuring the bioluminescent light) may be used to measure (e.g., via detection mechanism 210) a first bioluminescent signal from third test sample 205 (e.g. $L_1$) and a second bioluminescent signal from second test sample 204 (e.g., $L_2$). In a manner similar to that described above with respect to FIG. 1, a characteristic (e.g., strength, intensity, etc.) associated with the first bioluminescent signal and/or second bioluminescent signal may be proportional to the respective quantity and/or concentration of ATP and/or quantity of bacterial cells within third test sample 205 and/or second test sample 204, respectively. For example, 1000 colony forming units/milliliter (cfu/ml) may exist per fmole ATP (e.g., 500-1000 RLU's). If the bacteria, within third test sample 205, are susceptible to first antibiotic 206, the quantity of bacterial cells in third test sample 205 may be less than the quantity of bacterial cells in second test sample 204. The quantity of bacteria in third test sample 205 being less than that of second test sample 204 may cause the quantity and/or concentration of ATP, in third test sample 205, to be less than that of second test sample 204.

The lower quantity and/or concentration of ATP in third test sample 205 may cause a characteristic (e.g., strength, intensity, etc.) associated with a first bioluminescent signal (e.g., $L_1$), emitted from third test sample 205, to be less (or different) than a characteristic (e.g., strength, intensity, etc.) associated with a second bioluminescent signal (e.g., $L_2$), emitted from second test sample 204, by more than a second threshold (e.g., greater than 30 to 95% etc. less than the strength, intensity, etc. of the first bioluminescent signal). In such a case, the bacteria may be susceptible to the antibiotic, which may indicate that the antibiotic could be an effective treatment for the bacterial infection. Additionally, or alternatively, in the event that a difference between the characteristic (e.g., strength, intensity, etc.) associated with the first bioluminescent signal (e.g., $L_1$) and the characteristic (e.g., strength, intensity, etc.) associated with a second bioluminescent signal (e.g., $L_2$) is greater than a second threshold (e.g., $L_2-L_1>TH2$) (e.g., $TH2 \geq 30\%$ difference between $L_2$ and $L_1$) the bacteria may be susceptible to the antibiotic, which may indicate that the antibiotic could be an effective treatment for the bacterial infection.

However, a characteristic (e.g., strength, intensity, etc.) associated with the first bioluminescent signal (e.g., $L_1$) may not be less (or different) than a characteristic (e.g., strength, intensity, etc.) associated with the second bioluminescent signal (e.g., $L_2$) by more than a second threshold. In such a case, the bacteria present may not be susceptible to the antibiotic, which may indicate that the antibiotic is not an effective treatment for the bacterial infection. Additionally, or alternatively, in the event that the difference between a characteristic (e.g., strength, intensity, etc.) associated with the first bioluminescent signal (e.g., $L_1$) and a characteristic (e.g., strength, intensity, etc.) associated with the second bioluminescent signal (e.g., $L_2$) is not greater than a second threshold (e.g., $L_2-L_1 \leq TH2$), the bacteria may not be susceptible to the antibiotic, which may indicate that the antibiotic is not an effective treatment for the bacterial infection. In such a case, another assay 200 may be performed on one or more additional test sample (e.g., a fourth and fifth test sample, etc.), obtained from sample 101. Another, one or more different antibiotic may be added to one or more additional test sample to determine whether the bacteria is susceptible to the one or more different antibiotics in a manner similar to that described above. Assay 200 may also, or alternatively, be performed using a variety of different antibiotics to identify one or more antibiotics that are most effective against the bacterial infection. Additionally, or alternatively, a characteristic associated with the first and/or second bioluminescent signal may indicate and/or correspond to a severity of a bacterial infection, which may, for example, assist in prescribing the correct dosage of antibiotic.

The number of reagents, constituents, buffers, and/or components, illustrated in FIG. 2, is provided for explanatory purposes only and is not intended to be so limited. Additionally, or alternatively, assay 200 may include additional reagents, constituents, buffers, and/or components; fewer reagents, constituents, buffers, and/or components; different reagents, constituents, buffers, and/or components; or differently arranged reagents, constituents, buffers, and/or components than illustrated in FIG. 2.

Figure 3:
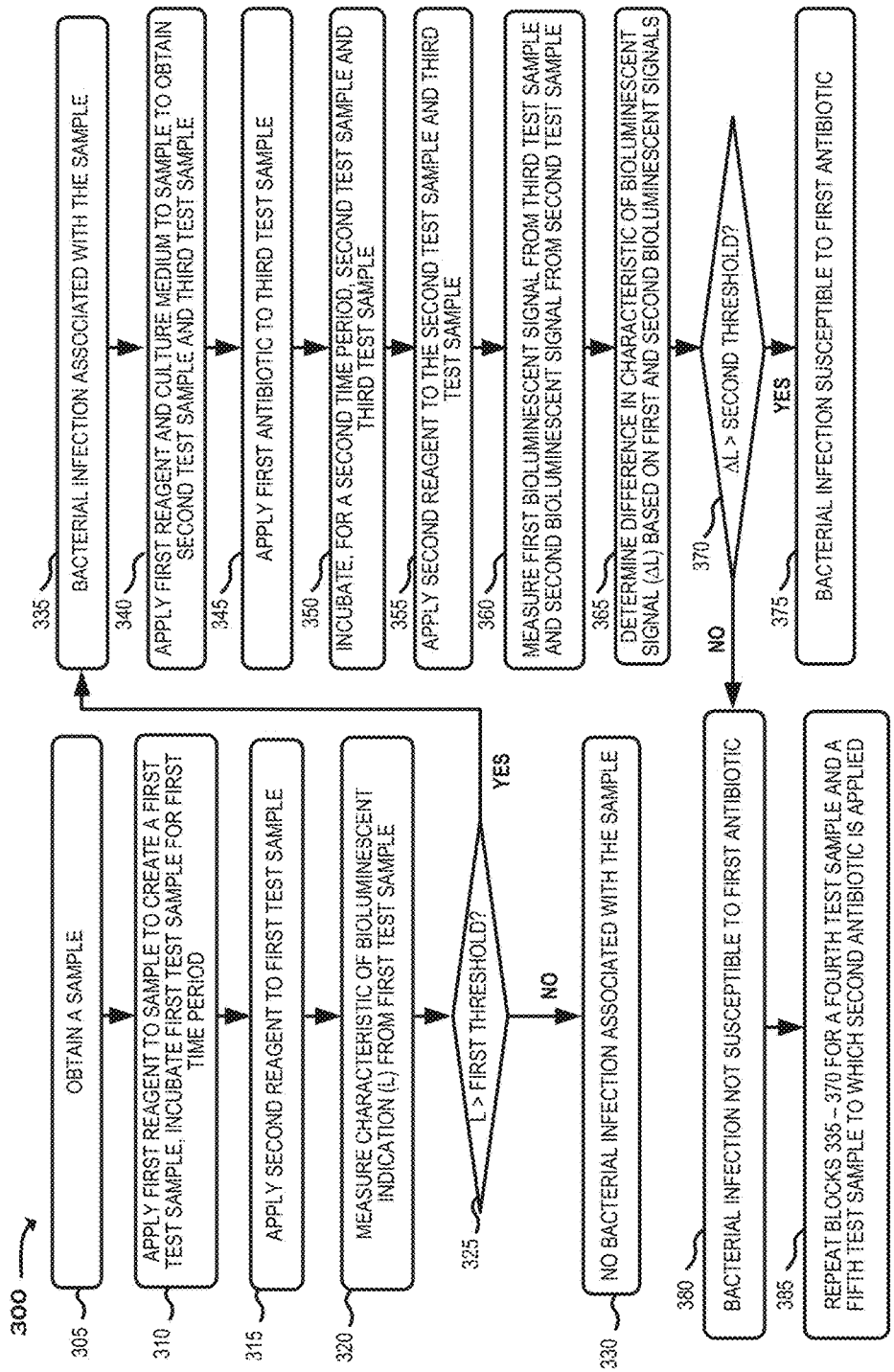
FIG. 3 is a flowchart of an example process for performing the assay of FIG. 1 and/or the assay of FIG. 2 according to an implementation described herein.

FIG. 3 is a flowchart of an example process 300 for performing assay 100 of FIG. 1 and/or assay 200 of FIG. 2 according to an implementation described herein. All or any steps and/or any combination of steps of process 300 (including any modified and/or additional steps not shown) may be completed within a time period ($T_{300}$) (e.g., ~20 to 50 minutes) that is less than a time period associated with a typical point of care visit ($T_{300}<T_{POC}$).

Process 300 may include, for example, steps 305 to 385. Step 305 may include obtaining sample 101 from a subject (e.g., a human subject, an animal subject, etc.). Step 310 may include applying first reagent 102 (e.g., 100 to 500 µL) to all or a portion of sample 101 (e.g., 1 to 20 µL) to create a first test sample 103. First reagent 102 may cause non-bacterial ATP to be released and removed from first test sample 103, in a manner similar to that described above with respect to FIG. 1 and may include one or more constituent and/or one or more ingredient as described above. First test sample 103 may incubate for a first incubation time period (e.g., ~1 to 15 minutes), which may be less than a first time period, which is less than the time period associated with a typical point of care visit.

Step 315 may include applying second reagent 104 (e.g., 100 to 500 µL) to first test sample 103. Second reagent 104 may be added to first test sample 103 to release the bacterial ATP from the bacterial cells therein and to cause bioluminescent light to be emitted, as described above with respect to FIG. 1 and may include one or more constituent and/or one or more ingredient as described above.

Step 320 may include measuring a bioluminescent indication (and associated characteristics) from first test sample 103 (e.g., based on released ATP, etc.). The bioluminescent indication may be detected and/or measured using test device 105 (e.g., a luminometer, a photodetector, a photodiode, handheld device, non-handheld device, and/or any device capable of detecting the emitted light).

Step 325 may include comparing a characteristic (e.g., strength, intensity, etc.) associated with the bioluminescent indication to a first threshold to determine if a bacterial infection (and/or its severity) is associated with sample 101. For example, test device 105 may indicate when the bioluminescent indication is not detected or a characteristic (e.g., signal strength, intensity, etc.) associated with the bioluminescent indication is not greater than a first threshold (e.g., >30,000 to 5 million RLU's) which may indicate that bacterial cells do not exist within sample 101 at a clinically significant level (e.g., at Step 330). In another example, test device 105 may indicate when the bioluminescent indication is detected or a characteristic (e.g., signal strength, etc.) associated with the bioluminescent indication is greater than a first threshold which may indicate bacterial cells exist within sample 101 at a clinically significant level (e.g., at Step 340). In the event that it is determined that a bacterial infection is associated with sample 101, steps 340-390 may be performed.

Step 340 may include obtaining second test sample 204 and third test sample 205 from sample 101 by applying first reagent 202 (e.g., 50 to 400 µL) and culture medium 203 (e.g., 50 to 300 µL). First reagent 202 applied to second test sample 204 and third test sample 205 may cause non-bacterial ATP to be released and removed, in a manner similar to that as described above with respect to FIGS. 1 and 2 and may similarly include one or more constituent and/or one or more ingredient, as described above. Culture medium 203 applied to second test sample 204 and third test sample 205 may promote the growth and robustness of the bacterial population, in a manner similar to that described above with respect to FIG. 2 and may similarly include one or more constituent and/or one or more ingredient, as described above. Step 345 may include applying first antibiotic 206 (e.g., Amoxicillin (e.g., 10 to 100 µg)) to third test sample 205. First antibiotic 206 may correspond to a concentration that first antibiotic 206 would approach in, for example, urine of the subject after being ingested, digested, and/or metabolized by the subject. With respect to implementations in which the sample is based on other than the urine of the subject (e.g., blood, wound exudate, optical fluid, cerebro—spinal fluid, vaginal fluid, mouth or throat, etc.) the concentration of first antibiotic 206 may correspond to the concentration that first antibiotic 206 would approach in the blood, wound exudate, optical fluid, etc. cerebro—spinal fluid, etc. of the subject after being ingested, digested, and/or metabolized by the subject.

Step 350 may include incubating second test sample 204 and the third test sample 205 for a second incubation time period, as described above with respect to FIG. 2. For example, the first incubation time period may be less than a second time period, which may be less than the time period associated with a typical point of care visit. Additionally, or alternatively, the total time for incubation (e.g., the first incubation time period plus the second incubation time period) may be less than the time period associated with a typical point of care visit.

Step 355 may include applying second reagent 207 (e.g., 100 to 500 µL) to second test sample 204 and third test sample 205. Second reagent 207 may, in a manner similar to that described above with respect to FIGS. 1 and 2, be added to second test sample 204 and third test sample 205 to release the bacterial ATP from the bacterial cells therein and to cause bioluminescent light to be emitted from each of second test sample 204 and/or third test sample 205. Second reagent 207 may similarly include one or more constituent and/or one or more ingredient, as described above.

Step 360 may include measuring a first bioluminescent signal (and associated one or more characteristic) from third test sample 205 and a second bioluminescent signal (and associated one or more characteristic) from second test sample 204 (e.g., based on released ATP, etc.). Test device 208 may be used to measure a first bioluminescent signal from third test sample 205 to determine a characteristic associated with the first bioluminescent signal and a second bioluminescent signal from second test sample 204 to determine a characteristic associated with the second bioluminescent signal. In a manner similar to that described above with respect to FIGS. 1 and 2, a characteristic (e.g., strength, intensity, etc.) associated with the first bioluminescent signal and/or a characteristic (e.g., strength, intensity, etc.) associated with the second bioluminescent signal may be proportional to the respective quantity and/or concentration of ATP and/or quantity of bacterial cells within third test sample 205 and/or second test sample 204, respectively. If the bacteria, within third test sample 205, are susceptible to first antibiotic 206, the quantity of bacterial cells in third test sample 205 may be less than the quantity of bacterial cells in second test sample 204.

Step 365 may include determining a difference and/or ratio between a characteristic (e.g., strength, intensity, etc.) associated with the first bioluminescent signal and a characteristic (e.g., strength, intensity, etc.) associated with the second bioluminescent signal (e.g., $\Delta L$) based on the first bioluminescent signal and the second bioluminescent signal.

Step 370 may include comparing the difference and/or ratio between a characteristic (e.g., strength, intensity, etc.) associated with first bioluminescent signal and a characteristic (e.g., strength, intensity, etc.) associated with the second bioluminescent signal (e.g., $\Delta L$) to a second threshold to determine if the bacterial infection is susceptible to first antibiotic 206. For example, a lower quantity and/or concentration of ATP in third test sample 205 may cause a characteristic (e.g., strength, intensity, etc.) associated with the first bioluminescent signal to be less than a characteristic (e.g., strength, intensity, etc.) associated with second bioluminescent signal emitted from second test sample 204, by more (or different) than a second threshold (e.g., greater than 15, 20, 25, 30, 35, 40%, etc. less than the second bioluminescent signal). In such a case, the bacteria may be susceptible to first antibiotic 206 (e.g., Step 375), which may indicate that first antibiotic 206 could be an effective treatment for the bacterial infection. Additionally, or alternatively, in the event that a difference between a characteristic (e.g., strength, intensity, etc.) associated with the first bioluminescent signal and a characteristic (e.g., strength, intensity, etc.) associated with the second bioluminescent signal is greater (or different) than a second threshold the bacteria may be susceptible to first antibiotic 206 (e.g., $\Delta L > TH2$) (e.g., $TH2 \geq 14$, 20, 25, 30, 35, 40% difference, etc.) (e.g., Step 380). This may indicate that first antibiotic 206 could be an effective treatment for the bacterial infection.

However, a characteristic (e.g., strength, intensity, etc.) associated with the first bioluminescent signal may not be less than a characteristic (e.g., strength, intensity, etc.) associated with second bioluminescent signal by more than the second threshold. In such a case, the bacteria present may not be susceptible to first antibiotic 206 (e.g., Step 380), which may indicate that first antibiotic 206 is not an effective treatment for the bacterial infection. Additionally, or alternatively, in the event that a difference and/or ratio between a characteristic (e.g., strength, intensity, etc.) associated with the first bioluminescent signal and a characteristic (e.g., strength, intensity, etc.) associated with the second bioluminescent signal is not greater (or different) than a second threshold, the bacteria may not be susceptible to first antibiotic 206 (e.g., Step 380). This may indicate that first antibiotic 206 is not an effective treatment for the bacterial infection.

Step 385 may include repeating Steps 340-380 for additional test samples (e.g., a fourth test sample, fifth test sample, etc.) to which additional, different antibiotics (e.g., second, third, etc.) are applied.

While series of blocks are identified with regard to FIG. 3, the order and/or timing of the blocks is not intended to be limiting and may be modified in other implementations. Further, non-dependent blocks may be performed concurrently, substantially concurrently, and/or in a different order. Additionally, or alternatively, in other implementations, process 300 may include additional steps, less steps, modified steps, and/or different steps than shown in FIG. 3.

Figure 4:
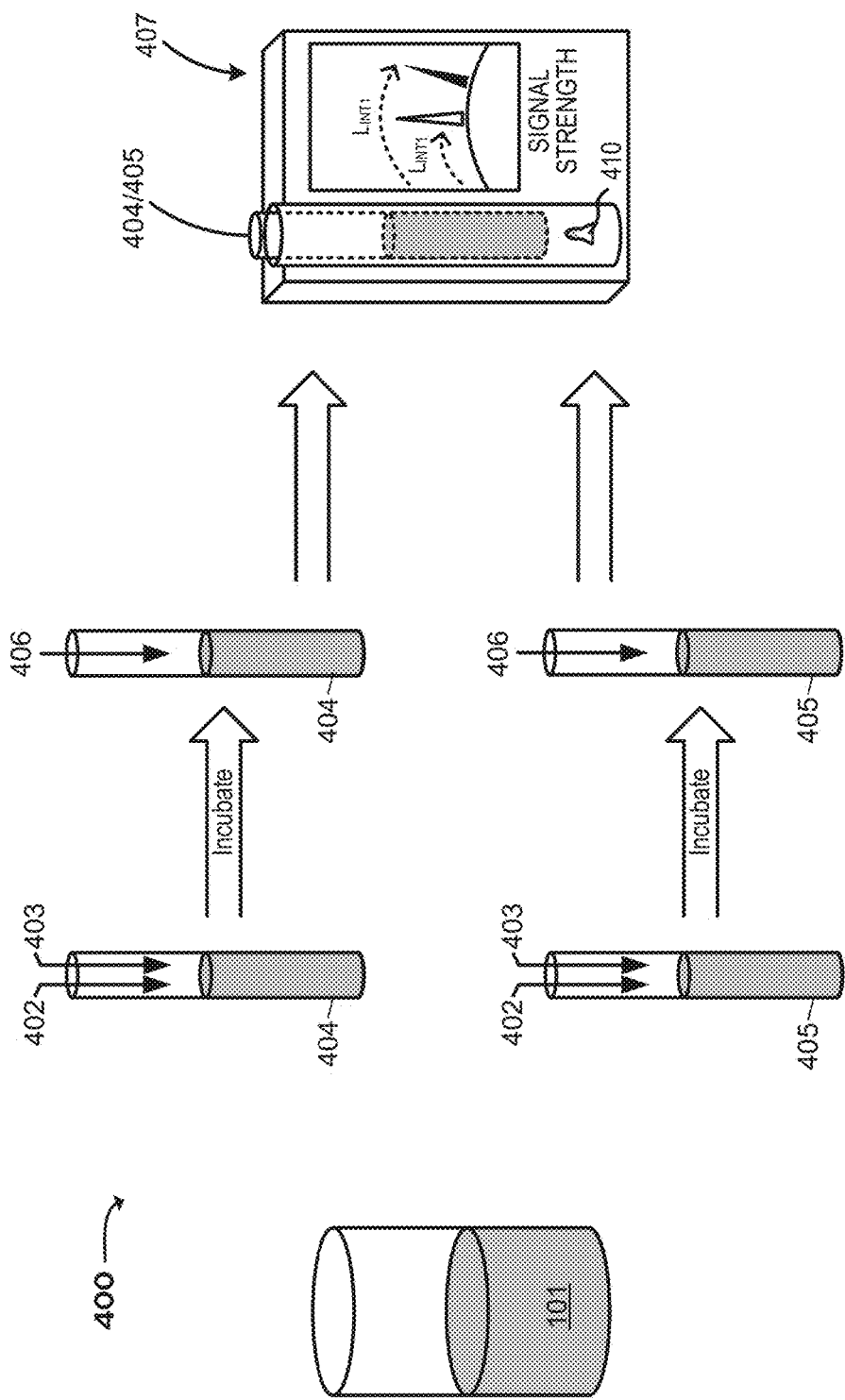
FIG. 4 is a diagram of an example assay performed on a sample obtained from a subject to detect a presence of a bacterial infection (or lack thereof)

FIG. 4 is a diagram of an example assay 400 that may be performed on sample 101 obtained from a subject to determine, confirm, and/or deny the detection of a presence of a bacterial infection (or lack thereof). Assay 400 may be completed (e.g., such that the presence of a bacterial infection may be determined) within a time period (e.g., $T_{400}$) (e.g., $\sim 30 \leq T_{400} < 60$ minutes) that is less than a time period associated with a point of care visit ($T_{400} < T_{POC}$). Additionally, or alternatively, all of assay 100, assay 200, and assay 400 may be completed within a time period that is less than a time period associated with a point of care visit ($T_{100} + T_{200} + T_{400} < T_{POC}$). In other implementations, assay 400 and assay 200 may be performed concurrently, substantially concurrently, or in parallel. For example, in such implementation assay 100 and assay 200 may be completed within a time period that is less than a time period associated with a point of care visit ($T_{100} + T_{200} < T_{POC}$) and assay 100 and assay 400 may be completed within a time period that is less than a time period associated with a point of care visit ($T_{100}+T_{400}<T_{POC}$).

Assay 400 may be performed if the results (e.g., positive or negative indication) of a previous assay (e.g., assay 100) are equivocal, for example, in the event that a characteristic (e.g., strength, intensity, etc.) associated with the bioluminescent indication (e.g., L) is a positive indication or negative indication, but not greater than (or inside) a confidence threshold (e.g., +/−25-50% of TH1). However, in the event that a characteristic (e.g., strength, intensity, etc.) associated with the bioluminescent indication (e.g., L) is greater than (or outside) a confidence threshold, assay 400 need not be or may not be performed. In such a case, if indication 107 (e.g., a negative indication, etc.) is outputted by test device 105, a medical practitioner may decide not to prescribe antibiotics to the subject. If indication 106 (e.g., a positive indication, etc.) is outputted by test device 105, another assay (e.g., assay 200 of FIG. 2) may be performed as described herein. Additionally, or alternatively, a medical practitioner may elect to perform assay 400 when the results of the previous assay are unequivocal. Additionally, or alternatively, assay 400 may be performed without any previous assay being performed on sample 101.

In the event that a characteristic (e.g., strength, intensity, etc.) associated with the bioluminescent indication (e.g., L) is a positive indication 106 or negative indication 107, but not greater than (or inside) a confidence threshold, assay 400 may be performed to determine the presence of a bacterial infection and/or confirm or deny such indication. For example, a first reagent 402 (e.g., 50 to 500 µL) and/or culture medium 403 (e.g., 50 to 300 µL) may be applied to all or a portion of sample 101 (e.g., 1 to 20 µL) to obtain a first confirmatory test sample 404 and second confirmatory test sample 405. In one example, first confirmatory test sample 404 and second confirmatory test sample 405 may be of approximately equal volume (e.g., 50 to 300 µL) to ensure that the concentration of any reagents, buffers, culture medium, etc. added to first confirmatory test sample 404 and second confirmatory test sample 405 are approximately equal between first confirmatory test sample 404 and second confirmatory test sample 405.

First reagent 402 may, in a manner similar to that described above with respect to FIGS. 1-3, cause non-bacterial ATP to be removed from first confirmatory test sample 404, and may similarly include one or more constituent and/or one or more ingredients as described above with respect to first reagent 102 and/or 202. Culture medium 403 may, in a manner similar to that described above with respect to culture medium 203 of FIGS. 2 and 3, promote the growth and robustness of the bacterial population (e.g., comprised of bacterial cells) within first confirmatory test sample 404 and second confirmatory test sample 405, and may similarly include one or more ingredient as described above.

Additionally, or alternatively, first confirmatory test sample 404 may be incubated for a first confirmatory incubation time period (e.g., $T_{confirm,inc1}$) and second confirmatory test sample 405 may be incubated for a second confirmatory incubation time period (e.g., $T_{confirm,inc2}$). The first confirmatory incubation time period (e.g., $T_{confirm,inc1}$) with first confirmatory test sample 404 may be less than the second confirmatory incubation time period (e.g., $T_{confirm,inc2}$) associated with second confirmatory test sample 405, which may be less than a third time period (e.g., $T_3$) (e.g., ~40≤$T_3$<60 minutes) that may be less than a time period associated with a typical point of care visit (e.g., $T_{confirm,inc2}<T_3<T_{POC}$). For example, first confirmatory incubation time period (e.g., $T_{confirm,inc1}$) may be ~0.5-15 minutes and second confirmatory incubation time period (e.g., $T_{confirm,inc2}$) may be ~25-40 minutes. However, these time periods and/or ranges are not intended to be limiting and other implementation may include different incubation time(s).

Additionally, or alternatively, first confirmatory test sample 404 may be incubated at a first incubation temperature and second confirmatory test sample 405 may be incubated at a second incubation temperature. For example, first confirmatory test sample 404 may be incubated at an ambient temperature (e.g., 12-30 degrees Celsius) and/or second confirmatory test sample 405 may be incubated at a body temperature (e.g., 35-38 degrees Celsius). These temperatures are not intended to be limiting and other implementations may include different incubation temperature(s).

Second reagent 406 (e.g., 100 to 500 µL) may, in a manner similar to that described above with respect to FIGS. 1-3, be added to first confirmatory test sample 404 and second confirmatory test sample 405 to release the bacterial ATP from the bacterial cells therein and to cause bioluminescent light to be emitted from each of first confirmatory test sample 404 and/or second confirmatory test sample 405, respectively. Second reagent 406 may similarly include one or more constituent and/or one or more ingredient, as described above.

Test device 407 (e.g., a luminometer, a photodetector, a photodiode, handheld device, non-handheld device, or any device capable of measuring the bioluminescent light) may be used to measure (e.g., via detection mechanism 410) a first confirmatory bioluminescent signal from first confirmatory test sample 404 (e.g. $L_{CONFIRM1}$) and a second confirmatory bioluminescent signal from second confirmatory test sample 405 (e.g., $L_{CONFIRM2}$). In a manner similar to that described above with respect to FIG. 1, a characteristic (e.g., strength, intensity, etc.) associated with the first confirmatory bioluminescent signal (e.g. $L_{CONFIRM1}$) and/or a characteristic (e.g., strength, intensity, etc.) associated with the second confirmatory bioluminescent signal (e.g., $L_{CONFIRM2}$) may be proportional to the respective quantity and/or concentration of ATP and/or quantity of bacterial cells within first confirmatory test sample 404 and/or second confirmatory test sample 405, respectively. For example, 1000 colony forming units/milliliter (cfu/ml) may exist per fmole ATP (e.g., 500-1000 RLUs). If bacteria cells are present in second confirmatory test sample 405, the quantity of bacterial cells in second confirmatory test sample 405 may be greater than the amount of bacterial cells in first confirmatory test sample 404. In such a case, a characteristic (e.g., strength, intensity, etc.) associated with the second confirmatory bioluminescent signal may be greater than a characteristic (e.g., strength, intensity, etc.) associated with the first confirmatory bioluminescent signal.

A difference and/or ratio between a characteristic (e.g., strength, intensity, etc.) associated with the second confirmatory bioluminescent signal and a characteristic (e.g., strength, intensity, etc.) associated with first confirmatory bioluminescent signal may be used to determine, confirm, and/or deny a presence of a bacterial infection (or lack thereof) in sample 101. This may be determined by comparison to a confirmatory threshold ($TH_{CONFIRM}$). For example, in the event that the difference and/or ratio of a characteristic (e.g., strength, intensity, etc.) associated with the second confirmatory bioluminescent signal (e.g., $L_{CONFIRM2}$) and a characteristic (e.g., strength, intensity, etc.) associated with the first confirmatory bioluminescent signal (e.g. $L_{CONFIRM1}$) is not greater than an confirmatory threshold (e.g., $L_{CONFIRM2}$ is less than 15, 20, 25, 30, 35, 40% etc. greater than $L_{CONFIRM1}$, $L_{CONFIRM2}-L_{CONFIRM1} \leq TH_{CONFIRM}$) (e.g., $TH_{CONFIRM}$ may be 15, 20, 25, 30, 35, 40% etc. difference between $L_{CONFIRM2}$ and $L_{CONFIRM1}$), it may be determined (and/or confirmed) that the bacterial cells do not exist within sample 101 at a clinically significant level, and a medical practitioner may decide not to prescribe antibiotics to the subject. In another example, in the event that the difference and/or ratio of a characteristic (e.g., strength, intensity, etc.) associated with the second confirmatory bioluminescent signal (e.g., $L_{CONFIRM2}$) and a characteristic (e.g., strength, intensity, etc.) associated with the first confirmatory bioluminescent signal (e.g. $L_{CONFIRM1}$) is greater than an confirmatory threshold (e.g., $L_{CONFIRM2}$ is 15, 20, 25, 30, 35, 40% etc. or more greater than $L_{CONFIRM1}$, $L_{CONFIRM2}-L_{CONFIRM1}>TH_{CONFIRM}$) it may be determined (and/or confirmed) that bacterial cells exist within sample 101 at a clinically significant level. If the presence of bacterial cells at a clinically significant level is confirmed, another assay (e.g., assay 200 of FIG. 2) may be performed on sample 101 to determine whether the bacterial infection within sample 101 is susceptible to an antibiotic.

The number of components, illustrated in FIG. 4, is provided for explanatory purposes only and is not intended to be so limited. Additionally, or alternatively, assay 400 may include additional components, fewer components, different components, or differently arranged components than illustrated in FIG. 4.

Figure 5:
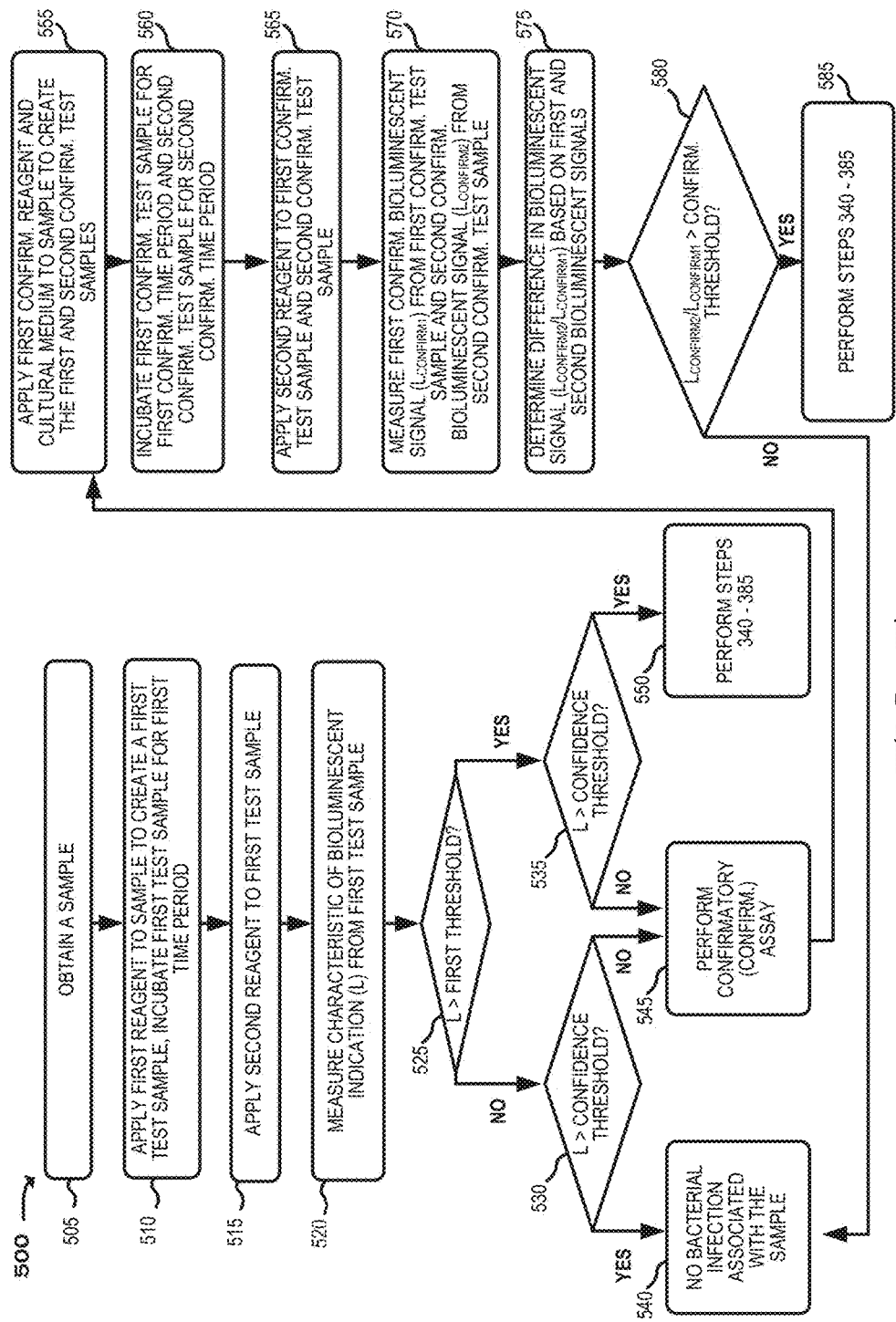
FIG. 5 is a flowchart of an example process for performing the assay of FIG. 1, the assay of FIG. 2, and/or the assay of FIG. 4 according to an implementation described herein.

FIG. 5 is a flowchart of an example process 500 for performing assay 100 of FIG. 1, assay 200 of FIG. 2, and/or assay 400 of FIG. 4 according to an implementation described herein. All or any steps and/or any combination of steps of process 500 (including any modified and/or additional steps not shown) may be completed within a time period that is less than a time period associated with a typical point of care visit.

Process 500 may include, for example, steps 505 to 585. Steps 505-525 may be performed in a manner similar to Steps 305-325, as described above with respect to FIG. 3.

Steps 530 and 535 may include comparing a characteristic (e.g., strength, intensity, etc.) associated with the bioluminescent indication (e.g., L) with a confidence threshold. For example, in the event that a characteristic (e.g., strength, intensity, etc.) associated with the bioluminescent indication is greater than the first threshold (e.g., 30,000 to 5 million RLUs) and greater than (and/or outside) the confidence threshold (e.g., +/−25-40% of the first threshold), another assay (e.g., assay 200) may be performed on sample 101 in a manner similar to that described in Steps 340-385 of process 300 in FIG. 3 (e.g., Step 550). In the event that a characteristic (e.g., strength, intensity, etc.) associated with the bioluminescent indication is not greater than the first threshold and greater than (or outside) the confidence threshold, it may be determined that no bacterial infection is associated with sample 101 (e.g., Step 540). However, in the event that a characteristic (e.g., strength, intensity, etc.) associated with the bioluminescent indication is greater or is not greater than the first threshold and not greater than (and/or inside) the confidence threshold, a confirmatory assay (e.g., assay 400) may be performed on sample 101 (e.g., Step 545).

To perform confirmatory assay 400, step 555 may include applying first reagent 402 (e.g., 50 to 500 μL) and culture medium 403 (e.g., 50 to 300 μL) to a portion of sample 101 (e.g., 1 to 20 μL) to create first confirmatory test sample 404 and second confirmatory test sample 405. First reagent 402 may cause non-bacterial ATP to be removed from first confirmatory test sample 404 and second confirmatory test sample 405, in a manner similar to that described herein with respect to FIG. 4 and may similarly include one or more constituent and/or one or more ingredient, as described herein. Culture medium 403 may promote the growth and robustness of the bacterial population (e.g., comprised of bacterial cells) within first confirmatory test sample 404 and second confirmatory test sample 405, in a manner similar to that described herein with respect to FIG. 4 and may similarly include one or more constituent and/or one or more ingredient, as described herein.

Step 560 may include incubating first confirmatory test sample 404 for a first confirmatory incubation time period (e.g., ~0.5 to 15 minutes) and incubating second confirmatory test sample 405 for a second confirmatory incubation time period (e.g., ~25 to 40 minutes). The first confirmatory time period may be less than the second confirmatory time period, which may be less than a time period associated with a typical point of care visit. Additionally, or alternatively, the total time for incubation occurring in process 500 may be less than a time period associated with a typical point of care visit. Additionally, or alternatively, first confirmatory test sample 404 may be incubated at a first confirmatory incubation temperature (e.g., ambient temperature) and second confirmatory test sample 405 may be incubated at a second confirmatory incubation temperature (e.g., body temperature).

Step 565 may include applying a second reagent 406 (e.g., 100 to 500 μL) to first confirmatory test sample 404 and second confirmatory test sample 405. Second reagent 406 may, in a manner similar to that described above with respect to FIG. 4, be added to first confirmatory test sample 404 and second confirmatory test sample 405 to release the bacterial ATP from the bacterial cells therein and to cause bioluminescent light to be emitted from each of first confirmatory test sample 404 and/or second confirmatory test sample 405. Second reagent 406 may similarly include one or more constituent and/or one or more ingredient as described herein.

Step 570 may include measuring a first confirmatory bioluminescent signal from first confirmatory test sample 404 and second confirmatory bioluminescent signal from second confirmatory test sample 405. Test device 407 may be used to measure the first confirmatory bioluminescent signal and/or the second confirmatory bioluminescent signal. In a manner similar to that described above with respect to FIG. 4, a characteristic (e.g., strength, intensity, etc.) associated with the first confirmatory bioluminescent signal and/or a characteristic (e.g., strength, intensity, etc.) associated with the second confirmatory bioluminescent signal may be proportional to the respective quantity and/or concentration of ATP and/or quantity of bacterial cells within first confirmatory test sample 404 and/or second confirmatory test sample 405, respectively.

Steps 575 and 580 may include determining a difference and/or ratio of a characteristic (e.g., strength, intensity, etc.) associated with the second confirmatory bioluminescent signal and a characteristic (e.g., strength, intensity, etc.) associated with the first confirmatory bioluminescent signal and comparing the difference and/or ratio to an confirmatory threshold. For example, in the event that the difference and/or ratio of a characteristic (e.g., strength, intensity, etc.) associated with the second confirmatory bioluminescent signal and a characteristic (e.g., strength, intensity, etc.) associated with the first confirmatory bioluminescent signal is not greater than a confirmatory threshold, it may be determined (and/or confirmed) that no bacterial infection is associated with sample 101 at a clinically significant level. In the event that the difference and/or ratio of a characteristic (e.g., strength, intensity, etc.) associated with the second confirmatory bioluminescent signal and a characteristic (e.g., strength, intensity, etc.) associated with the first confirmatory bioluminescent signal is greater than a confirmatory threshold, it may be determined (and/or confirmed) that bacterial cells exist within sample 101 at a clinically significant level. In such a case, another assay (e.g., 200) may be performed on sample 101 in a manner similar to that of Steps 340-385 of process 300 (e.g., Step 585).

While series of blocks are identified with regard to FIG. 5, the order of the blocks are not intended to be limiting and may be modified in other implementations. Further, non-dependent blocks may be performed in parallel. Additionally, or alternatively, in other implementations, process 500 may include additional steps, less steps, modified steps, and/or different steps than shown in FIG. 5. Additionally, or alternatively, all or any steps of process 500 may be completed within a time period that is less than a time period associated with a typical point of care visit.

The following example is intended to illustrate the present invention without limitation. To perform assay 100, a sample 101 (e.g. urine) may be obtained from a subject (e.g., a human subject, an animal subject, etc.). 150-300 µL of first reagent 102 may be added to 1 to 20 µL of sample 101 to create a first test sample 103. First reagent 102 may include 10-100 mM of Tris Acetate as a buffer, 0.0001 to 0.1% Benzethonium Chloride, and 0.5 to 4 Units/ml of Apyrase. First reagent 102 may cause non-bacterial ATP to be released and removed from first test sample 103 (as described herein) and first test sample 103 may incubate for ~5 minutes (e.g., first incubation time period).

At the end of the first incubation time period, 150-500 µL of second reagent 104 may be added to first test sample 103. Second reagent 102 may include 10-100 mM of Tris Acetate as a buffer, 5 to 30 mg/L of Luciferase, 5 to 30 mg/L of Luciferin, and 0.1 to 0.5% Chlorhexidine di-gluconate. Second reagent 104 may be added to first test sample 103 to release the bacterial ATP from the bacterial cells therein and to cause bioluminescent light to be emitted.

A bioluminescent indication (and its associated strength) may be measured from first test sample 103 (e.g., based on released ATP caused by second reagent 104, etc.). In this example, the bioluminescent indication may be detected and/or measured using a Berthold Junior Luminometer. The strength of the bioluminescent indication may be proportional to the quantity of bacterial cells in sample 101, for example, it may be found that 1000 colony forming units/milliliter (cfu/ml) may exist per fmole ATP (e.g., 500-1000 RLU's). In one example, the strength of the bioluminescent indication was measured to be 72,257 RLU's and the quantity of bacterial cells was determined to be 80,000 cfu/ml (by a gold standard reference methodology).

The strength of the bioluminescent indication may be compared to a first threshold to determine if a bacterial infection is associated with sample 101. The first threshold may be, for example, 30,000 RLU's. If the strength of the bioluminescent indication is not greater than 30,000 RLU's it may be found that bacterial cells do not exist within sample 101 at a clinically significant level. However, if the strength of the bioluminescent indication is greater than 30,000 RLU's it may be found that bacterial cells do exist within sample 101 at a clinically significant level. In this example, the strength of the bioluminescent indication was found to be 72,257 RLU's, and thus was above the first threshold.

The strength of the bioluminescent output signal may be compared with a confidence threshold. In this example, the confidence threshold may be +/−30% of 30,000 RLU's. In the event that the strength associated with the first bioluminescent indication is greater than 30,000 RLU's and greater than (and/or outside) +/−30% of 30,000 RLU's, another assay (e.g., assay 200) may be performed on sample 101, as described below. However, in the event that the strength associated with the bioluminescent indication is greater or is not greater than 30,000 and is not greater than (and/or inside) +/−30% of 30,000 RLU's, a confirmatory assay (e.g., assay 400) may be performed on sample 101.

Despite the strength of the bioluminescent indication in this example, the following is an example to illustrate confirmatory assay 400, and is not intended to be limiting. To perform confirmatory assay 400, 50-500 µL of first reagent 402 and 50 to 300 µL of Tryptic Soy Broth (culture medium 403) may be applied to 1 to 20 µL of sample 101 to create first confirmatory test sample 404 and second confirmatory test sample 405. First reagent 402 may include 10 to 100 mM of Tris Acetate as a buffer, 0.0001 to 0.1% of Benzethonium Chloride, and 0.5 to 4 Units/ml of Apyrase. First reagent 402 may cause non-bacterial ATP to be removed from first confirmatory test sample 404 and second confirmatory test sample 405, in a manner similar to that described herein. Culture medium 403 may promote the growth and robustness of the bacterial population within first confirmatory test sample 404 and second confirmatory test sample 405, in a manner similar to that described herein.

First confirmatory test sample 404 may be incubated for ~5 mins at ambient temperature and second confirmatory test sample 405 may be incubated for ~40 mins at 37 degrees Celsius.

After incubation, 150-500 µL of second reagent 406 may be applied to first confirmatory test sample 404 and second confirmatory test sample 405. Second reagent 406 may include 10 to 100 mM of Tris Acetate as a buffer, 2 to 30 mg/L of Luciferase, 2 to 30 mg/L of Luciferin, and 0.1 to 0.5% of Chlorhexidine di-gluconate. Second reagent 406 may, in a manner similar to that described herein, be added to first confirmatory test sample 404 and second confirmatory test sample 405 to release the bacterial ATP from the bacterial cells therein and to cause bioluminescent light to be emitted from each of first confirmatory test sample 404 and/or second confirmatory test sample 405.

A Berthold Junior Luminometer may be used to measure a first confirmatory bioluminescent signal from first confirmatory test sample 404 and second confirmatory bioluminescent signal from second confirmatory test sample 405. A strength associated with the first confirmatory bioluminescent signal and/or a strength associated with the second confirmatory bioluminescent signal may be proportional to the respective quantity of bacterial cells within first confirmatory test sample 404 and/or second confirmatory test sample 405, respectively. For example, 1000 colony forming units/milliliter (cfu/ml) may exist per fmole ATP (e.g., 500-1000 RLU's). In this example, the first confirmatory bioluminescent signal from first confirmatory test sample 404 was measured to be 26215 and the second confirmatory bioluminescent signal from second confirmatory test sample 404 was measured to be 54698. Thus, the quantity of bacterial cells within first confirmatory test sample 404 was determined to be ~20,000 cfu/ml and the quantity of bacterial cells within second confirmatory test sample 404 was determined to be ~50,000 cfu/ml.

A difference of the strength associated with the second confirmatory bioluminescent signal and the strength associated with the first confirmatory bioluminescent signal may be determined and compared with the difference and/or ratio to a confirmatory threshold. In this example, the confirmatory threshold may be >30% of the first confirmatory signal. Further, in this example, the difference of the strength associated with the second confirmatory bioluminescent signal and the strength associated with the first confirmatory bioluminescent signal was found to be 208% and thus, is greater than the confirmatory threshold. This may confirm that bacterial cells exist within sample 101 at a clinically significant level (e.g., 1000 to 10,000 cfu/ml) and that an assay to determine antibiotic susceptibility (e.g., assay 200) may be necessary. It has been found that assay 400 may be performed within 40 minutes under these parameters.

To perform assay 200 to determine antibiotic susceptibility of a bacterial infection within the sample, a second test sample 204 and third test sample 205 may be obtained from sample 101 by applying 50 to 400 μL of first reagent 202 and 50 to 300 μL of culture medium 203 to 1 to 20 μL of sample 101 to create second test sample 204 and to 1 to 20 μL of sample 101 to create third test sample 205. First reagent 202 may include 10 to 100 mM of Tris Acetate as a buffer, 0.0001 to 0.1% of Benzethonium Chloride, and 0.5 to 4 Units/ml of Apyrase. First reagent 202 may cause nonbacterial ATP to be released and removed, in a manner similar to that as described herein. Culture medium 203 may include 50 to 300 μL of Tryptic Soy Broth. Culture medium 203 may be applied to second test sample 204 and third test sample 205 and may promote the growth and robustness of the bacterial population, in a manner similar to that described herein.

First antibiotic 206 may be applied to third test sample 205. In this example, first antibiotic 206 may include 10 to 100 μg of Amoxicillin. Second test sample 204 and the third test sample 205 may then be incubated for ~40 minutes at 37 degrees Celsius.

After incubation, second reagent 207 (e.g., 100 to 500 μL) may be applied to second test sample 204 and third test sample 205. Second reagent 207 may include 10 to 100 mM of Tris Acetate as a buffer and 2 to 30 mg/L of Luciferase, 2 to 30 mg/L of Luciferin, and 0.1 to 0.5% of Chlorhexidine di-gluconate. Second reagent 207 may be added to second test sample 204 and third test sample 205 to release the bacterial ATP from the bacterial cells therein and to cause bioluminescent light to be emitted.

A Berthold Junior Luminometer may be used to measure a first bioluminescent signal (and associated strength) from third test sample 205 and a second bioluminescent signal (and associated strength) from second test sample 204 (e.g., based on released ATP, etc.). In a manner similar to that described above, the strength associated with the first bioluminescent signal and/or the strength associated with the second bioluminescent signal may be proportional to the respective quantity and/or concentration of ATP and/or quantity of bacterial cells within third test sample 205 and/or second test sample 204, respectively. In this example, 1000 colony forming units/milliliter (cfu/ml) may exist per fmole ATP (e.g., 500-1000 RLU's). In this example, the strength of the first bioluminescent signal was measured to be 66,823 RLU's and the strength of the second bioluminescent signal was measured to be 62,535 RLU's. Thus, the quantity of bacteria cells in third test sample 205 was ~62,000 cfu/ml and the quantity of bacteria cells in the second test sample 204 was ~67,000 cfu/ml.

In the event that the bacteria, within third test sample 205, are susceptible to first antibiotic 206, the quantity of bacterial cells in third test sample 205 may be less than the quantity of bacterial cells in second test sample 204. In this example, quantity of bacteria cells within third test sample 205 (e.g., ~62,000 cfu/ml) was found to be less than the quantity of bacteria cells within second test sample 204 (e.g., ~67,000 cfu/ml).

Additionally, or alternatively, a difference between the strength associated with the first bioluminescent signal and the strength associated with the second bioluminescent signal (e.g., $\Delta L$) may be compared to a second threshold to determine if the bacterial infection is susceptible to first antibiotic 206. The second threshold may be, for example >30% difference. In this example, $\Delta L$ was 7.5% and was not greater than a 30% difference. Thus, the bacteria within test sample 205 may not be susceptible to first antibiotic 206 which indicates that Amoxicillin (e.g., 10-100 μg) may not be an effective treatment for the bacterial infection. It has been found that assay 200 may be performed within ~40 minutes under these parameters.

If Amoxicillin (10-100 μg) was not shown to be susceptible to first antibiotic 206, one or more additional assays including additional test samples (e.g., a fourth test sample, fifth test sample, etc.) and additional susceptibility tests of different antibiotics may be performed.

A kit may include one or more device, apparatus, hardware, systems elements, material, substance, reagents, constituents, etc. needed to perform one or more of assay 100, 200, and/or 400. For example, the kit may contain one or more container and/or instrument for taking one or more samples from a subject and creating one or more test samples. Additionally, or alternatively, the kit may include one or more container that includes one or more constituents of a first reagent, second reagent, and/or culture medium, as described herein with respect to FIGS. 1-5. Additionally, or alternatively, the kit may include a test device (e.g., a luminometer, a photodetector, a photodiode, handheld device, non-handheld device, and/or any device capable of detecting the emitted light, etc.) that may measure a bioluminescent indication and/or signal from one or more test sample. The elements of the kit are not intended to be limiting. In other implementations, the kit may include additional reagents, devices, devices, apparatuses, materials, substances, hardware, systems elements, etc. that may be used to perform assay 100, 200, and/or 300.

The foregoing description provides illustration and description, but is not intended to be exhaustive or to limit the implementations to the precise form disclosed. Modifications and variations are possible in light of the above disclosure or may be acquired from practice of the embodiments.

It should be emphasized that the terms "comprises"/"comprising" when used in this specification are taken to specify the presence of stated features, integers, steps or components but does not preclude the presence or addition of one or more other features, integers, steps, components or groups thereof.

Even though particular combinations of features are recited in the claims and/or disclosed in the specification, these combinations are not intended to limit the disclosure of the embodiments. In fact, many of these features may be combined in ways not specifically recited in the claims and/or disclosed in the specification. Although each dependent claim listed below may directly depend on only one other claim, the disclosure of the embodiments includes each dependent claim in combination with every other claim in the claim set.

No element, act, or instruction used in the present application should be construed as critical or essential to the implementations unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method for determining whether bacteria in a sample obtained from a subject at a point of care in a clinical setting is susceptible to an antibiotic, within a time period associated with a point of care, the method comprising:
    applying, at a first time, to a portion of the sample, a first reagent to create a first test sample from which non-bacteria based background Adenosine triphosphate (ATP) is removed by the first reagent;
    incubating the first test sample for a first time period;
    applying a second reagent to the first test sample to release ATP from bacterial cells when the first test sample includes bacterial cells;
    measuring a bioluminescent indication from the first test sample based on bacterial released ATP to determine a characteristic associated with the bioluminescent indication; comparing the characteristic associated with the bioluminescent indication to a confidence threshold;
    correlating whether the sample includes bacteria by comparing the characteristic associated with the bioluminescent indication to a first threshold;
    applying, to at least a portion of the sample, the first reagent and a culture medium to create a first confirmatory test sample and a second confirmatory test sample from which non-bacteria based background ATP has been removed by the first reagent;
    incubating the first confirmatory test sample for a first confirmatory time period and at a first temperature and the second confirmatory test sample for a second confirmatory time period that is greater than the first confirmatory time period and at a second temperature;
    applying the second reagent to the first confirmatory test sample at the end of the first confirmatory time period and the second confirmatory test sample at the end of the second confirmatory time period, to release ATP from bacterial cells when the first confirmatory test sample and second confirmatory test sample include bacterial cells;
    measuring a first confirmatory bioluminescent signal from the first confirmatory test sample based on ATP released from bacteria to determine a characteristic associated with the first confirmatory bioluminescent signal, measuring a second confirmatory bioluminescent signal from the second confirmatory test sample based on ATP released from bacteria to determine a characteristic associated with the second confirmatory bioluminescent signal;
    determining a difference between the characteristic associated with the first confirmatory bioluminescent signal and the characteristic associated with the second confirmatory bioluminescent signal;
    determining, at a second time, whether bacteria are is present in the sample by comparing the difference between the characteristic associated with the first confirmatory bioluminescent signal and the characteristic associated with the second confirmatory bioluminescent signal to a confirmatory threshold,
    a difference between the first time and the second time being less than the time period associated with the point of care visit;
    applying, to at least a portion of the sample, the first reagent and a culture medium to create a second test sample and a third test sample, from which non-bacteria based background ATP is removed by the first reagent;
    applying a first antibiotic to the third test sample;
    incubating the second test sample and the third test sample for a second time period and at a third temperature;
    applying a second reagent to the second test sample and the third test sample at the end of the second time period;
    measuring a first bioluminescent signal from the second test sample based on ATP released form bacteria to determine a characteristic associated with the first bioluminescent signal and a second bioluminescent signal from the third test sample based on ATP released from bacteria to determine a characteristic associated with the second bioluminescent signal;
    determining a difference between the characteristic associated with the first bioluminescent signal and the characteristic associated with the second bioluminescent signal;
    correlating at a third time, that the bacteria are susceptible to the first antibiotic by comparing the difference between the characteristic associated with the second bioluminescent signal and the characteristic associated with the first bioluminescent signal to a second threshold,
    a difference between the first time and the third time being less than the time period associated with the point of care visit; and
    correlating the first and second signals with the presence or absence of the bacterial infection.

2. The method of claim 1, where the first temperature is ambient temperature and the second temperature is 36-38 degrees Celsius.

3. The method of claim 1, further comprising:
    determining that the sample does not contain the bacteria when the difference between the characteristic associated with the first confirmatory bioluminescent signal and the characteristic associated with the second confirmatory bioluminescent signal is not greater than the confirmatory threshold.

4. The method of claim 1, further comprising:
    determining that the sample does contain the bacteria when the difference between the characteristic associated with the first confirmatory bioluminescent signal and the characteristic associated with the second confirmatory bioluminescent signal is greater than the confirmatory threshold.

5. The method of claim 1, where the characteristic of the bioluminescent indication corresponds to a strength associated with the bioluminescent indication, the characteristic associated with the first confirmatory bioluminescent signal corresponds to a strength of the first confirmatory bioluminescent signal, and the characteristic associated with the second confirmatory bioluminescent signal corresponds to a strength of the second confirmatory bioluminescent signal.

6. The method of claim 1, where the first temperature is 36-38 degrees Celsius.

7. The method of claim 1, where the step of measuring the bioluminescent indication, and the step of measuring the first and second bioluminescent signal are performed with a test device.

8. The method of claim 1, further comprising:
determining that the bacteria are is susceptible to the first antibiotic when the difference between the characteristic associated with the second bioluminescent signal and the characteristic associated with the first bioluminescent signal is greater than the second threshold;
determining that the bacteria are is not susceptible to the first antibiotic when the difference between the characteristic associated with the second bioluminescent signal and the characteristic associated with the first bioluminescent signal is not greater than the second threshold.

* * * * *